United States Patent
Filatov et al.

(10) Patent No.: US 6,500,799 B2
(45) Date of Patent: Dec. 31, 2002

(54) WOUND DRESSING

(76) Inventors: Vladimir N. Filatov, 1 Botkinsky St., 4, flat 19, Moscow 125284 (RU); Vladimir Ryltsev, Nijegorodskya St., 13 a, flat 41, Moscow 109029 (RU); Zidkiyahu Simenhaus, Misgav Am 12165, Misgav (IL)

( * ) Notice: Subject to any disclaimer, the term of this patent is extended or adjusted under 35 U.S.C. 154(b) by 0 days.

(21) Appl. No.: 09/816,862

(22) Filed: Mar. 26, 2001

(65) Prior Publication Data

US 2002/0012692 A1 Jan. 31, 2002

Related U.S. Application Data

(63) Continuation-in-part of application No. 09/288,635, filed on Apr. 9, 1999, now abandoned.

(51) Int. Cl.$^7$ .......................... A61K 38/00; A61K 9/70; A61K 38/43; A61K 47/00
(52) U.S. Cl. .......................... 514/2; 424/44.1; 424/94.2; 424/94.61; 424/94.64; 424/443; 424/444; 424/445; 424/446; 424/447; 424/449; 514/769; 514/772; 514/772.1; 514/781

(58) Field of Search ................................ 424/443, 444, 424/445, 446, 447, 449, 94.1, 94.2, 94.61, 94.64; 514/2, 3, 4, 769, 772, 772.1, 781

(56) References Cited

U.S. PATENT DOCUMENTS 5,015,387 A  *  5/1991  Nemori et al. .............. 210/638

FOREIGN PATENT DOCUMENTS

GB        2 240 040       *  7/1991

* cited by examiner

Primary Examiner—Allen J. Robinson
Assistant Examiner—Frank Choi
(74) Attorney, Agent, or Firm—Morgan, Lewis & Bockius LLP

(57) ABSTRACT

The invention provides a method for preparing a wound dressing, comprising activating a textile carrier to form between about 0.026 and 0.06 mg-equiv. of aldehyde groups per gram of carrier, impregnating the activated carrier in a solution of at least one bioactive enzyme and drying the same, whereby there is produced a wound dressing from which the bioactive enzyme is releasable in effective amounts for a period of at least 3 days upon the dressing being brought into contact with a moist surface.

11 Claims, 1 Drawing Sheet

Figure No. 1
Figure No. 2
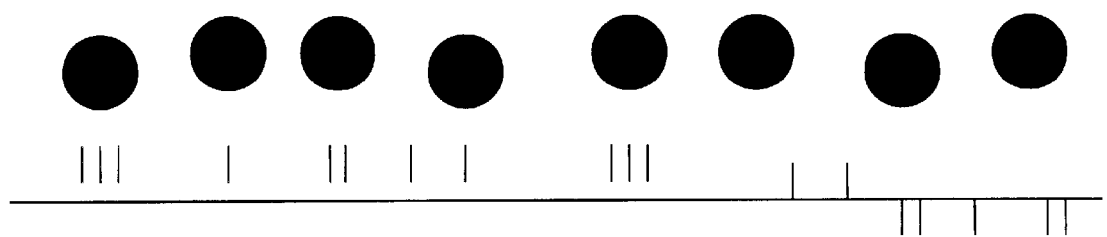
Figure No. 3
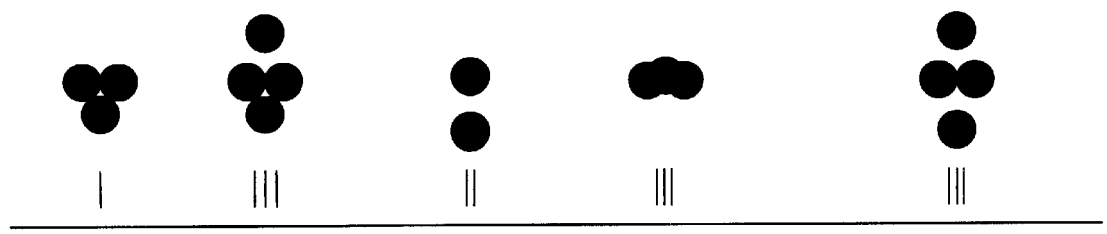

WOUND DRESSING

The present specification is a continuation-in-part of U.S. Ser. No. 09/288,635, filed Apr. 9, 1999, now abandoned.

FIELD OF THE INVENTION

The present invention relates to wound dressings and methods for the preparation thereof. More specifically, the present invention relates to a method for preparing dressings for treating pyo-necrotic and infected wounds, topical ulcers and for prophilaxis of suppuration of infected wounds.

DESCRIPTION OF RELATED ART

It is known in medical practice to use native proteolytic enzyme preparations for treating pyo-inflammatory diseases. However, said enzymes are expensive and scarce. Regardless of certain effectiveness, said enzymes are not resistant against inhibitors which are contained in wound discharge, or against pH and temperature changes. During release of native enzymes into wound exudates, said enzymes are quickly inactivated, therefore treatment requires a considerable amount of enzymes.

For reduction of the need for enzymes, a dressing was created which has a prolonged action, contains immobilized enzymes on textile material and is resistant to environmental influence, but has a lower therapeutically activity than the activity of native enzymes.

A method is known in the art for preparing a material having immobilized enzymes which comprises the following steps:

Activating the textile carrier by introducing functional groups into the carrier until the amount of reactive functional groups reaches 0.0625–3.125 mg-equiv. of reactive functional groups per gram of a carrier.

Treating the activated carrier with a solution of enzymes in buffer solutions having a pH of 6.5–7.5 at room temperature for 8–16 hours; and washing and drying the active textile carrier.

Materials having a biological activity and having a prolonged action have been prepared by said method with an immobilized enzyme. Said material is used for treating wounds and burns (laid-open German Patent No. 4000797, C 12N 11/02, Jul. 18, 1991).

Said method is disadvantageous in that the enzyme activity is reduced with its chemical immobilization. It results in producing a dressing having lower therapeutical effectiveness in comparison with native enzyme.

Similarly, known in the art is a method for preparing a material having immobilized enzyme, which comprises the following steps:

activating the textile carrier;

treating the carrier with solution of trypsin (0.05%) in a phosphate buffer having a pH of 6.5–6.7 at module of 5–6 for 2 hours; and the obtained cloth is squeezed out, dried and treated by solution of insulin having an activity of 4.0–4.4 units per ml (Russian Patent No. 2062113, A 61 L 15/38, Jun. 20, 1996.

The materials prepared by said method produce a long necrolytic, anti-inflammatory, anti-toxic and draining effect, but the method for preparing the material is time consuming and the obtained cloth has a lower therapeutical effectiveness of native enzyme.

Similarly known in the art is a method for the preparation of a material containing immobilized enzyme which comprises the following steps:

activating the textile carrier by forming therein reactive functional groups containing 0.5% w/w (corresponds to 0.0625 mg-eq. of aldehyde per gram of carrier)—to 25% w/w (corresponds to 3.125 mg-eq. of aldehyde per gram of carrier).

treating the carrier with a trypsin solution, 0.02%–0.05% w/w in a phosphate buffer, pH 6.5–7.5 at room temperature for 8–16 hours in order to form a covalent bond between the activated carrier, i.e., the oxidized textile, and the enzyme.

The cloth is then squeezed and washed with water until no biological activity can be detected, and dried at room temperature (GB PATENT No. 2,240,040 A, Dated Jul. 24, 1991.

The materials prepared by said method have necrolytic, anti-inflammatory, anti-toxic and draining properties, but the preparation method is time consuming, effective for 4 days (only mentioned but even not claimed), and have a lower therapeutical effectiveness than the native enzyme. These activity duration and effectiveness are obtained by incorporating into the textile fabric a relatively high amount of functional groups: 0.5% w/w to 25% w/w as aforesaid.

Due to the high amount of functional groups and as a result of the binding nature of the immobilized enzyme(s) to the activated cloth, a relatively high amount of the immobilized enzyme is bound. The lower therapeutical effectiveness of the cloth, despite the relatively high amount of enzyme(s) incorporated, is a result of the binding nature of the immobilized enzyme(s) as described and explained herein.

The bonding nature of the bioactive enzyme(s) and/or other biological active substance(s) to the textile carrier is determined by the degree of oxidation, i.e., the amount of functional group incorporated in the textile carriers.

Dialdehyde cellulose is a macromolecule with aldehyde moities randomly distributed over the chain as shown in FIG. 1 appended hereto.

The horizontal line seen in said figure represents the cellulose molecule and the vertical lines represent the aldehyde groups.

It is known in the art of enzymology engineering that the process of immobilizing large quantities of protein onto a carrier leads to steric hindrance, which can impede chemical reactions.

The ability of a carrier to capture and hold molecules such as enzymes' and/or other bioactive substances could be expressed as a ratio between the degrees of the oxidation of the carrier to the amount of protein.

As described in GB Patent 2,240,040, the oxidation degree of a carrier varies from 0.5% (respectively 0.0625 mg.-equiv per 1 (one) gram) to 25% (3,125 mg.-equiv. per 1 gram); and the amount of immobilized enzymes varies from 0,02 per 1 (one) gram of the 0.5% oxidized carrier to 0.5 per 1 (one) gram of the 25% oxidized carrier. It is clear that a carrier with a 0.5% degree of oxidation is capable of binding 0.02% of protein, and the capability of a carrier with a 25% degree of oxidation is to bind 0.5% of protein. Thus the ratio between the oxidation degree of the carrier and the amount of protein, i.e., the ability limit of an oxidized carrier to bind molecules, such as enzymes' or other bioactive substances' molecules as per the GB Patent, is expressed as follows:

The Lower limit is: *0.5/0.02=25 (*respectively 0.065 mg.-equiv./gm)

The Upper Limit is: *25.0/0.5=50 (*respectively 3.125 mg.-equiv./gm)

As mentioned above, the binding nature of the enzyme(s) or other bioactive substances is determined by the concentration of aldehyde groups in a carrier. Due to the large amount of aldehyde in dialdehyde cellulose at 25% degree of oxidation, as specified in the GB publication, all the trypsin, and the enzyme(s), are bound by covalent azomethine bridges HC=N. The energy of an azomethine bond varies from 393 to 583 kJ/mole. The trypsin molecules in such respectively large amounts cover the Dialdehyde cellulose chain as a continuous monomolecular layer and form a shield over a significant portion of the aldehyde groups, as represented by FIG. 2 appended hereto.

It is known in the art that huge molecules of protein, (e.g., trypsin—a proteolytic enzyme—has the molecular weight of 24,000 Da), inhibits and delays the functional groups of the protein and the carrier from positioning in a close proximity and thus from interacting, i.e., forming azomethine bridges. This suggests the need for a large excess of aldehydic groups over amino ones during the chemical binding of large amount of protein. Thus, the penetration, i.e., binding, of large molecules of protein such as trypsin, into an oxidized carrier and the maturation, i.e. immobilization and stabilization of the enzyme, is a slow process, which requires respectively 8–16 hours, as specified in the GB publication. During the 8–16 hours of the maturation treatment process most of the protein immobilized substance molecules are bound unevenly even randomly, covalently bound into the oxidized fabric, with a maximal concentration on top layer and a minimal below it.

Since azomethine bridges cannot be split by the wound discharge, the therapeutic effect of such dressing(s) could be attributed to the hydrolysis of dialdehyde cellulose at high oxidation levels as well as to the dissolution of oligomeric fragments of dialdehyde cellulose chain with chemically bound trypsin.

Known in the art is a method for the calculation of the hydrolysis of protein and/or other bioactive substances, incorporated in a dialdehyde cellulose carrier, as it is released from the carrier itself. According to the calculations due to the method, as per the equation of rate of release:

$$K[A]^a[B]^b[C]^c \ldots [Z]^z \ldots$$

Where K is the rate constant, which is an invariable occurring of a chemical reaction, i.e. how fast the original (starting) substances disappear by hydrolysis.

[A], [B], [C] ... [Z] ..., stands for the current existing concentration of the reagent, and a, b, c, ... z ..., are the so-called orders of the reactions. The results are as follows:

Referring to the dressing produced according to the GB publication, from a dressing at 5% degree of oxidation and respectively 0.02% of protein covalently bound, 50% of the total amount of the protein incorporated is releasable during 36 hours, and in next 36 hours an additional 25% of the initial amount is released, i.e., during 72 hours 75% of the total amount is releasable. From a dressing of 25% degree of oxidation and respectively 0.5% of protein covalently bound, only 77% of the protein incorporated is releasable. 50% were released during the first 24 hours, and during the next 48 hours 22%–27% were released, i.e., during 72 hours 72%–77% of the initial total amount is releasable.

From the aforesaid, it will be understood that because of the dissorption process, 95%–97%, almost all of the incorporated enzyme(s) and/or another bioactive substance(s) other than enzymes, is gradually released for at least 3 (three) days.

SUMMARY OF THE INVENTION

The object of the present invention is to provide a material to be used as a dressing containing an enzyme compound and having a therapeutical effectiveness of native enzyme and prolonged action.

BRIEF DESCRIPTION OF THE DRAWINGS

FIGS. 1, 2, and 3 are schematic representations which are used to describe the invention as more fully detailed hereinafter.

DETAILED DESCRIPTION OF THE INVENTION

The oxidation method for the preparation of the textile material carrier according to the present invention is carried out as follows: the textile fabric is immersed in a solution containing functional groups. By utilizing a wringer or a padder of two or three rollers, the textile material is pressed between the rollers, or by a press under similar conditions. The material is dried subsequently by forced hot air, oven drying, or in a vacuum chamber. The fabric is then brought into contact with a solution containing enzyme(s) or other biological active substances for impregnating or coating. The impregnated fabric is then pressed by a wringer, or a padder, between two or three rollers; the solvent is separated from the treated textile material by pressing, squeezing, evaporation, or centrifugation, etc. The obtained material is dried by utilizing forced hot air, oven drying, vacuum chamber, etc., at 18° C.–38° C. The speed of the process is monitored.

For example, the fabric is immersed at room temperature in a solution, which contains functional groups. Solution weight to carrier weight ratio—is 3.3. In a continuous process as described hereinbelow the excess solution is pressed out and carrier material(s) is dried. The excess solution is pressed out and the active compounds spread uniformly into the volume of the textile carrier and on the surface of the fabric, by being pressed by a wringer between two rollers at 25 Kg–35 Kg pressure per 1 sq. cm. Thus the fabric is partially dried. The carrier material(s) is dried by utilizing a drier, i.e., a hot air blowing chamber or a hot drum chamber, heated up to 50° C., or a vacuum chamber. Then the material is immersed in a tub containing a solution of enzyme(s) and/or biologically active substance(s), at ratio—solution weight to carrier weight) of 3.3. Solvent excess is 1.8. The impregnated fabric is then pressed by a wringer between two rollers, of 10 cm diameter and of 30 cm length, at 25 Kg pressure per 1 sq. cm. The enzyme(s) and/or the biologically active substance(s) are equally and uniformly incorporated and spread into the volume of the textile carrier and onto the surface of the fabric, while the excessive solvent, (1.8 L of the 3.3 L of the bath ratio) are pressed out. The so-called maturation of the treated and partially dried fabric is 2 hours only, during which the completion of chemical and sorption immobilization is achieved. During the 2 hours of the immobilization process, about 20% of the substances are chemically bound to the carrier, and about 80% by sorption. These 80% are released, step-by-step, into the wound discharge as native species thus ensuring a high level of therapeutical effectiveness. The 20% above-mentioned are, also, gradually released. Finally the textile material(s) is dried by a drier, i.e., a hot air blowing chamber or a hot drum chamber, heated up to 18° C.–38° C. The speed of the drying process is synchronized.

With this state of the art in mind, there is now provided according to the present invention a method for preparing a wound dressing, comprising activating a textile carrier to form between about 0.026 and 0.06 mg-equiv. of aldehyde groups per gram of carrier, impregnating said active carrier in a solution of at least one bioactive enzyme and drying the same, whereby there is produced a wound dressing More specifically, the present invention provides a method for preparing a wound dressing, by activating a textile carrier to form a carrier comprising between 0.208% w/w (corresponding to 0.026 mg-equiv. of aldehyde groups per gram of carrier) and 0.48% w/w (corresponding to 0.06 mg-equiv. of aldehyde groups per gram of carrier) equally incorporated into the fabric; and by binding enzymes and other bioactive substances, other than enzymes, by immersing the said activated carrier in a solution of at least two different enzymes, or one enzyme and at least one biological active substance other than an enzyme, even from different classes, as indicated below, impregnating or coating the carrier and drying the same, whereby there is produced a wound dressing from which said bioactive enzyme(s) and the other the biological active substances other than enzymes are releasable in effective amounts for a period of at least 3 days upon said dressing being brought into contact with a moist surface. As aforesaid, during the 2 hours of the immobilization process, ~20% of the co-immobilized substances are chemically bounded to the carrier, and ~80% by sorption forces. These 80% of the enzyme(s) and/or other bioactive substances, bound by sorption, upon being brought into contact with a wound surface are slowing released, step by step, into the wound discharge as native species and 20%, above mentioned, are also gradually released. Thus the present invention provides a high level of therapeutical effectiveness close to native enzyme(s).

The present invention also provides a wound dressing comprising an activated textile carrier containing between about 0.026 and 0.06 mg-equiv. of aldehyde groups per gram of carrier, said wound dressing being impregnated with at least one bioactive enzyme, whereby said active enzyme is releasable from said wound dressing in effective amounts for a period of at least 3 days upon said dressing being brought into contact with a moist surface.

In preferred embodiments of the present invention said wound dressing comprises between about 0.3 and 1.5 mg of bioactive enzyme per gram of carrier.

As described hereinabove the oxidation degree of a carrier, produced according to the present invention, varies from 0.208% (respectively 0.026 mg.-equiv per 1 (one) gram) to 0.48% (0.060 mg.-equiv. per 1 gram. The amount of immobilized enzymes; bound per 1 (one) gram of the 0.208% oxidized carrier is 0.033% per 1 (one) gram of the carrier. Similarly 0.066% up to 1 (one) gram of the 0.48% oxidized carrier. It is clear that a carrier with a 0.208% to 0.048% degree of oxidation is capable of binding 0.066% of protein. Thus the ratio between the oxidation degree of the carrier and the amount of protein, i.e., the ability limit of an oxidized carrier to bind molecules, such as enzymes' or other bioactive substances' molecules as per the present invention could be expressed as follows:

The Lower limit is: *0.208/0.033=6.30 (*respectively ~0.026 mg.-equiv./gm)

The Upper Limit is: *0.48/0.066=7.27 (*respectively ~0.060 mg.-equiv./gm)

At such a low degree of oxidation, as described in the present invention, i.e., 0.208% to 0.48%, only a small part of the enzyme(s) ~20% is bound covalently while the majority ~80% is bound by sorption, to the 20% of protein molecules (chemically) covalently bound. This is schematically shown in FIG. 3.

A The energy of the chemo-sorption is 12.5 kJ/mole to 50 kJ/mole.

Due to the weakness of the chemo-sorption bonds, the enzyme(s) and other bioactive substances could be easily split by the wound discharge itself. The enzyme(s) and/or other bioactive substance(s) is gradually released from the dressing into the injured site, by a dissorption kinetic process, and effectively epurate it from any debris and decay. By the aforesaid dissorption, therapeutical activity, about 95%–97%, almost all of the incorporated enzyme(s) and/or other bioactive substance(s) other than enzymes, is gradually released for at least 3 (three) days. Thus, the dressing produced according to the present invention provides an incessant activity with a high therapeutical activity of the material, close to native species effectiveness.

In contradistinction to the material provided according to the GB patent, which is covalently bound, it is possible, because of the nature of the sorption binding, as per the present invention, to bind and to co-immobilize to the same carrier two bioactive substances, even of different classes, and to achieve a higher prolonged therapeutical effectiveness, close to native species.

The obtained material(s), which comprise an enzyme and a bioactive substance, have a prolonged activity of antibacterial properties, effective for at least 3 days.

The antimicrobial activity of the obtained materials, prepared according to Example 7 as described hereinbelow, was tested on lawns of several bacteria: Staphylococcus aureus, S. epidermidis, pseudomonas aeruginosa, Entrobacter spp., Proteus; Peptococcus, Peptosteptococcus, Veillonella, Fubacterius, B. fragilis, etc., inoculated on agar plats, by placing a sample of about 2 $cm^2$ on the surface of the plat, and measurement of the inhibition zone after growth of the bacteria for 18 hours at 37° C. After 72 hours, the inhibition zone was measured. The results are summarized below in Table 1 and Table 2.

The data set forth in the Tables herein is presented as follows:

Abs—The figures indicate the number of the tests, i.e., agar plates, at a minimum distance of 12 mm of growth inhibition beyond the matrix.

TABLE NO. 1

Inhibition of clinical stains by dressing materials prepared according to Ex. 7

| Microorganism | No. of Tests | Dressing with Trypsin Abs | % | Dressing with Decamethoxine Abs | % | Dressing with Trypsin and Decamethioxine Abs | % |
|---|---|---|---|---|---|---|---|
| S. aureus | 32 | 6 | 18.75 | 28 | 87.50 | 31 | 96.87 |
| S. epidermidis | 46 | 8 | 17.39 | 40 | 86.95 | 45 | 97.82 |

TABLE NO. 1-continued

Inhibition of clinical stains by dressing materials prepared according to Ex. 7

| Microorganism | No. of Tests | Dressing with Trypsin Abs | % | Dressing with Decamethoxine Abs | % | Dressing with Trypsin and Decamethioxine Abs | % |
|---|---|---|---|---|---|---|---|
| Ps. Aeruginosa | 18 | 2 | 11.11 | 12 | 66.66 | 16 | 88.88 |
| Enterobacter spp. | 17 | 1 | 5.88 | 12 | 70.58 | 15 | 83.33 |
| Proteus | 16 | 0 | 0 | 10 | 62.50 | 14 | 87.50 |

TABLE NO. 2

Inhibition of non-spore-forming anaerobic microorganism by dressing materials prepared according to Ex. 7

| Microorganism | No. of Tests | Dressing with Trypsin Abs | % | Dressing with Decamethoxine Abs | % | Dressing with Trypsin and Decamethioxine Abs | % |
|---|---|---|---|---|---|---|---|
| Peptococcus | 14 | 9 | 64.28 | 1 | 7.14 | 10 | 7.142 |
| Pepto-steptococcus | 17 | 11 | 64.70 | 2 | 11.76 | 13 | 76.47 |
| Veillonella | 9 | 6 | 66.66 | 0 | 0 | 8 | 88.88 |
| Other | 19 | 12 | 63.15 | 2 | 10.52 | 16 | 84.21 |
| Fubacterius | 24 | 19 | 79.16 | 0 | 0 | 22 | 91.66 |
| B. Fragilis | 8 | 5 | 62.50 | 0 | 0 | 7 | 87.50 |

The material(s) prepared by the described method as per the present invention was tested under clinical conditions being used for treating 715 patients having pyo-necrotic diseases, frostbites, tropic ulcers, etc. A control group of patients having pyo-necrotic diseases, frostbites, tropic ulcers, etc. has been treated as follows: 350 patients With dressings prepared according to the GB publication method; 331 patients with dressings comprises native enzyme; and 339 patients by a conventional method, i.e., by using a hypertonic salt solution containing antiseptic.

Following a preliminary surgical treatment such as dissection of the pyo-necrotic area, opening of pockets, dissection of intersections, and forming a single cavity, the hereinabove dressings, treated as specified hereinbelow, were locally applied to the wound(s).

The claimed material(s), in form of pad(s), was topically applied to the wound. Thus being brought into contact with a wound discharge, or a moist surface of the patient(s)' body itself, the claimed material(s) was activated for at least 3 (three) days. Only if it was necessary, because of abstain of discharge from the wound(s), the pads were impregnated with saline, i.e., sodium chloride solution 0.9%, also called physiologic salt solution.

The dressings prepared as per the GB publication and the dressings with the native enzyme as well, or cotton wool (lint), were locally applied, in form of pads, to the wound site(s) and impregnated with a physiologic salt solution in order to activate the biological compound.

The conventional method—a hypertonic solution containing antiseptic added to a dressing, applied to the wound.

The results of the comparative studies on treatment of wounds with deferent dressings materials are presented in Table No. 3 and Table No. 4 hereto as an example of the healing rate of the average required days for healing, and the rate of the healing acceleration in the course of recovery.

TABLE NO. 3

Treatment of tropic ulcers of the lower extremities with deferent dressing materials

| Treatment | Ulcer epuration Days in average | Healing acceleration % | Granulation and Epithelialization Days in Average | Healing Acceleration % | Complete Healing of the wounds Days in average | Healing Acceleration % |
|---|---|---|---|---|---|---|
| Conventional Method | 7.5 | Basis | 12 | Basis | 20.4 | Basis |
| Dressing as per the GB Patent | 5.7 | 24% | 10.1 | 14.9% | 18.5 | 9.3% |
| Dressing as per the present invention | 2.4 | 68% | 4.5 | 62.5% | 15 | 26.5% |

It has been found that when the claimed material(s) is applied the period of healing is reduced to around 15 (fifteen) days, whereas the period for complete treatment while curing by a dressing prepared as per the GB publication was 18.5 days, and by using a conventional method, as described hereto, 20.4 days, e.g., application of the claimed material enables to accelerate the course of treatment 1.2 times as much on the average in comparison to the dressing prepared according to the GB publication, and 1.33 times as much on the average in comparison to a conventional treatment.

TABLE NO. 4

Treatment of patients having pyo-necrotic diseases, frostbites, tropic ulcers, etc.
Period of treatment (days)

| Characteristic of the process of treatment | A dressing comprising trypsin and mexidole | A dressing comprising trypsin | Dressing prepared as per the GB publication | Dressing comprising native enzyme | Dressing with a hypertonic salt solution and antiseptic |
|---|---|---|---|---|---|
| Complete Purification of wounds and emergence of granulation | 2.0 ± 0.2 days | 3.2 ± 0.3 days | 4.5 ± 0.2 days | 7.7 ± 0.5 days | 9.6 ± 0.6 days |
| Complete healing of the wound from the beginning of treatment | 10.0 ± 0.5 days | 12.0 ± 1.0 days | 15.0 ± 2.2 days | 20.0 ± 1.5 days | 26.0 ± 2.2 days |

It has been found that when the claimed material(s) is applied the period of healing is reduced as follows:

By using a dressing(s) prepared according to the present invention, comprising trypsin and mexidole the period of healing is reduced to around 10 days and by using a dressing comprising trypsin the period of healing is reduced to 12, whereas the period for complete treatment while curing by a dressing prepared as per the GB publication was around 15 days, and by using a conventional method, as described hereto, about 26 days. That is, application of the claimed material, which contains trypsin and mexidole, enables to accelerate the course of treatment 1.5–1.6 times as much on the average, in comparison to the dressing prepared according to the GB publication, and 2.6 times as much on the average in comparison to a conventional treatment. Application of the claimed material, which contains trypsin enables to accelerate the course of treatment 1.25 times as much on the average in comparison to a dressing prepared according to the GB publication, and 2 times as much on the average in comparison to a conventional treatment.

In preferred embodiments of the present invention the degree of oxidation of said textile carrier is less than 0.5%, i.e. between 0.208% w/w and 0.48% w/w, This is in contradistinction to the percentage of oxidation generally used in the prior art which is in the range of about 40% w/w; and that used in previously mentioned Russian publication, which is between 1% and 25% w/w; and even that used in the previously mentioned GB publication which is between 0.5% and 25% w/w (0.5% corresponds to 0.0625 mg-eq/g of aldehyde; and 25% corresponds to 3.125 mg-eq/g of aldehyde).

In preferred embodiment of the present invention at least one enzyme is trypsin.

In especially preferred embodiments of the present said activated carrier is impregnated in solution of at least two bioactive enzymes, e.g., trypsin and lysozyme.

In other preferred embodiments of the present invention said activated carrier is impregnated in a solution of at least one bioactive enzyme and one hormone, e.g., trypsin and insulin.

In other preferred embodiments of the present invention said activated carrier is impregnated in a solution of at least one bioactive enzyme and one biologically active substance, e.g., trypsin and decamethoxine.

In other preferred embodiments of the present invention said activated carrier is impregnated in a solution of at least one bioactive enzyme and one biological active substance, e.g., trypsin and mexidole.

In preferred embodiments of the present invention the degree of oxidation of said textile carrier, at a bath ratio 3.3 and a weight ratio of 0.033% of each of said enzymes and other biological active substances in reference to the carrier (w/w); allowing said ingredients to be incorporated into the carrier until an increase of additional 150% to the original weight of the carrier has been achieved.

In one preferred aspect of the present invention said textile carrier is formed of cotton gauze activated by oxidation with sodium periodate to prepare a dialdehyde cellulose.

In another preferred aspect of the present invention said textile carrier is formed of a knitted fabric from caproamide fibers activated with hydrochloric acid, followed by the addition of glutaric aldehyde said knitted fabric with aldehyde groups.

The invention also provides a wound dressing comprising an activated textile carrier containing between about 0.0026 and 0.06 mg-equiv. of aldehyde groups per gram of carrier, said wound dressing being impregnated with at least one bioactive enzyme, whereby said active enzyme is releasable from said wound dressing in effective amounts for a period of at least 3 days upon said dressing being brought into contact with a moist surface.

In preferred embodiments of the present invention said wound dressing comprises comprising between about 0.3 and 1.5 mg of bioactive enzyme per gram of carrier.

The wound dressing prepared according to the new method of the present invention is different from all known prior art materials in that the content of enzyme in said material is conditioned by sorption characteristics of the textile carrier. A high therapeutical activity of the material close to the activity of native enzyme proves that there is no chemical bond between the enzyme and the textile carrier. The material has a prolonged action of at least three days; therefore the enzyme is sorbed on the textile carrier and is gradually released in small doses into the wound.

When materials to be used as dressings are produced according to the prior art, including impregnation of non-active textile carrier by solution of enzyme, they do not have prolonged therapeutical activity. When applied to the wound, said material releases the main part (up to 95%) of the enzyme into the wound in the first 5–10 minutes and the entire content of the dressing is inactivated within one hour.

The dressing prepared according to the Russian patent mentioned hereinbefore are released and inactivated within 24 hours.

The dressing prepared according to the GB patent mentioned hereinbefore, which comprise a relatively high amount of enzyme are released and inactivated within 4 days, but still at a low therapeutical effectiveness.

Thus, it was surprising and unexpected to find that activating a textile carrier to form between 0.026 and 0.05 mg-equiv. of dialdehyde per gram of carrier to form impregnation thereof with at least one bioactive enzyme resulted in the production of a wound dressing from which said bioactive enzyme is releasable in effective amounts for a period of at least 3 days upon said dressing being brought into contact with a moist surface.

While the invention will now be described in connection with certain preferred embodiments in the following examples and with reference to the appended figures so that aspects thereof may be more fully understood and appreciated, it is not intended to limit the invention to these particular embodiments. On the contrary, it is intended to cover all alternatives, modification and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of proving what is believed to be the most useful and readily understood description of formulation procedures as well as of the principles and conceptual aspects of the invention.

In the figures referred to hereinbefore:

FIG. 1 is a schematic representation of a dialdehyde cellulose with aldehyde moities randomly distributed over the chain;

FIG. 2 is a schematic representation of a dialdehyde cellulose chain as a continuous monomolecular layer wherein trypsin molecules form a shield over a significant portion of the aldehyde groups; and FIG. 3 is a schematic representation of a dialdehyde cellulose chain according to the present invention, wherein only a small part of the enzymes are bound covalently, while the majority is bound by sorption to the protein molecules which are covalently bound to the chain.

EXAMPLE 1

Medical cotton gauze was activated by oxidation with sodium periodate to prepare dialdehyde cellulose as follows:

3.3 L of water were poured into a reactor, mixed with a stirrer and 6.0 g of iodic acid were added thereto. The same amount of water was poured into another reactor and 1.90 g of sodium hydroxide were added to the water using a stirrer. Both solutions were agitated until the crystals of the acid and sodium hydroxide were dissolved within 5–15 minutes. The solutions were then poured into a reactor, agitated for 3–6 minutes to give a sodium periodate solution have a pH of 5.0.

1 Kg of medical cotton gauze was placed into the resulting solution and held (activated) at room temperature for 14 hours in the dark. After activating, the cloth was squeezed out, washed with 4×10 L of water and squeezed again.

As a result of activation, the cotton cloth (dialdehyde cellulose), acquires aldehyde group containing 0.04 mg-equiv. per gram of the textile carrier.

A solution of trypsin is prepared in phosphate buffer having a pH of 5.5 as follows:

0.33 g of trypsin were added to 3.3 L of the prepared phosphate buffer solution, stirring until it was completely dissolved. The activated textile carrier was reacted by impregnation. The resulting material was held in air for 2 hours and dried.

EXAMPLE 2

A knitted fabric from caproamide fibers was activated to prepare a dressing as follows:

40 L of 3M hydrochloric was poured into a reactor and 1.0 kg of knitted fabric from polycaproamide fibers was placed therein. The temperature was adjusted to 60° C. and the fabric was kept at this temperature for 4 hours. Upon completion of hydrolysis, excess hydrochloric and was cooled and discarded. The knitted fabric was washed with water until no hydrochloric acid was observed in washings.

38.4 L of 5% a glutaric aldehyde was poured into the reactor, and 1.0 kg of the knitted fabric subjected to hydrolysis was placed therein. The temperature of glutaric aldehyde solution was adjusted to 50° C. and maintained for 4 hours. Then the glutaric aldehyde solution was cooled and poured out and after that the fabric was washed with water until there was no smell of glutaric aldehyde.

As a result of activation, the knitted fabric acquires aldehyde groups containing 0.05 mg-equiv., per gram of textile fabric.

The further treatment is carried out following the procedure of Example 1.

EXAMPLE 3

Medical cotton gauze was activated to obtain dialdehyde cellulose following the procedure of Example 1, except that 7.5 9 of iodic acid and 1.25 g of sodium hydroxide were used. The resulting aldehyde cellulose contains 0.05 mg-equiv. of aldehyde groups per gram of a carrier.

Then a solution of trypsin is prepared in a phosphate buffer following the procedure of Example 1, and a solution of insulin in distilled water, with the activity of 3.6 units per ml, is prepared.

The prepared solutions are stirred in equal volume ratio, and the textile carrier is activated with the obtained mixture by impregnation. Then the resulting material is held in air for 2 hours and dried.

EXAMPLE 4

A knitted fabric from caproamide fibers was activated following the procedure of Example 2, except that 40 L of 3M of hydrochloric acid and 32 L of 5% a glutaric aldehyde were used. A resulting knitted fabric acquired aldehyde groups containing 0.05 mg-equiv. per gram of textile fabric.

Solutions of trypsin and insulin were prepared following the procedure of Example 3. The prepared solutions are stirred in equal volume ratio, and the textile carrier is activated with the obtained mixture by impregnation. Then the resulting material is held in air for 2 hours and dried.

EXAMPLE 5

Medical cotton gauze was activated to obtain dialdehyde cellulose following the procedure of Example 1, except that 9.0 g of iodic acid and 1.5 g of sodium hydroxide were used. The resulting aldehyde cellulose contains 0.06 mg-equiv. of aldehyde groups per gram of a carrier.

Then solutions of trypsin and lysozyme are prepared in phosphate buffer following the procedure of Example 1.

The prepared solution is stirred in equal volume ratio, and the textile carrier is activated with the obtained mixture by impregnation. The resulting material is then kept in air for 2 hours and dried.

EXAMPLE 6

A knitted fabric from caproamide fibers was activated following the procedure of Example 2, except that 32 L of 3M of hydrochloric acid and 25.6 L of 5% a glutaric aldehyde were used. A resulting knitted fabric acquires aldehyde groups containing 0.04 mg-equiv. per gram of textile fabric.

Solutions of trypsin and lysozyme were prepared following the procedure of Example 5. The prepared solutions are stirred in equal volume ratio, and the textile fabric is activated with the obtained mixture by impregnation. Then the resulting material is held in air for 2 hours and dried.

EXAMPLE 7

Medical cotton gauze was activated to obtain dialdehyde cellulose containing 0.026 mg-equiv. of aldehyde groups (i.e., 0.20% w/w) per gram of a carrier, by using the procedure described in example 3.

A solution of trypsin was prepared in phosphate buffer following the procedure described in example 1. For 1.0 Kg of the oxidized textile carrier to be impregnated with the bioactive ingredients, 0.33 gram of trypsin was added to 1.65 L of buffer solution at pH 5.5, and the resulting mixture was stirred until completely dissolved.

For 1.0 Kg of the oxidized textile carrier to be impregnated with the bioactive ingredients, 0.33 gram of decamethoxine (i.e., 1.10-decamethylene -bis-n, n-dimethylmentihoxycarbonylmethyl, ammonium dichloride) was added to each 1.65 L of buffer solution at pH 5.5, and the resulting mixture was stirred until completely dissolved.

The two solutions were combined in a ratio of 1/1 and the textile carrier was immersed in the resulting solution for activation. The carrier was then kept 2 hours at room temperature, dried partially between two rollers at a pressure of 25 Kg per 1 sq. cm, or a press under similar pressure and dried by utilizing forced hot air, hot oven etc. etc.

EXAMPLE 8

Medical cotton gauze was activated to obtain dialdehyde cellulose containing 0.035 mg-equiv. of aldehyde groups (i.e., 0.28% w/w) per gram of carrier, by using the procedure described in example 3.

Then a solution of trypsin was prepared in a phosphate buffer as described in example 1. Per each 1.0 Kg oxidized textile carrier to be impregnated with the bioactive ingredients, 0.33 gram of trypsin was added to 1.65 L buffer solution at pH 5.5, and the resulting mixture was stirred to complete dissolution.

Per each 1.0 Kg oxidized textile carrier to be impregnated with the bioactive ingredients, 0.33 gram of antioxidant mexidole (i.e., 3-hydroxy-6-methyl-2ethypyridine succinate) was added to 1.65 L buffer solution at pH 5.5, and the resulting mixture was stirred to complete dissolution.

The two solutions were combined in equal volumes, and the textile carrier was immersed in the mixture for activation and impregnation. The resulting material was aerated during 2 hours, partially dried between two rollers at a pressure of 25 Kg per 1 sq. cm, or a press under similar pressure; and dried by utilizing forced hot air, hot oven etc. .

The dressings prepared according to the methods described in Examples 1–8, were tested under clinical conditions, treating 715 patients having pyo-necrotic diseases and topical ulcers.

After a preliminary treatment, the dressing, impregnated with a physiologic salt solution of sodium chloride or with a solution of an antiseptic (0.5% a chlorohexidine bigluconate) were applied on the pyo-necrotic wound or incorporated into the pyo-necrotic cavity. Dressing was replaced every 1–2 day.

The clinical study and the cytotoxic analysis have proven that when the dressing according to the present invention are applied, the period of inflammation in soft tissues is reduced, the pyo-necrotic egesta becomes serofibrinous, the completion of phagocytosis in wounds occurs rapidly and proliferation of fibroblasts is more active. Further more, active material continued to be released from each of the dressing for a period in excess of 72 hours. Therefore the dressing of the present invention, when applied, enable the acceleration of period of purification of pyo-necrotic wounds, and the formation of granulation tissue of by cicatricial tissue and of epithelialization. These dressings further enable the earlier application of stitches and reduce the period of treatment.

It has been found that the dressings of the present invention are applied, the period of the first phase of treating is reduced from 10–29% in comparison with treating with the material having chemically immobilized enzyme. Formation of granulation and epithelialization are accelerated 1.5–2 times.

It will be evident to those skilled in art that the invention is not limited to the details of the foregoing illustrative examples and that the present invention may be embodied in other specific forms without departing from the essential attributes thereof, and it is thereof desired that the present embodiments and examples be considered in all respects as illustrative and not restrictive, reference being made to the appended claims, rather than to the foregoing description, and all changes which come within the meaning and range of equivalency of the claims are thereof intended to be embraced therein.

What is claimed is:

1. A method for preparing a wound dressing, comprising activating a textile carrier by immersing the carrier in a solution containing functional groups to affect the oxidation thereof and pressing said activated textile to uniformly spread said functional groups into the volume of the carrier and on the surface thereof to form between about 0.026 and 0.06 mg equivalent of aldehyde groups per gram of carrier, impregnating said active carrier in a solution of at least one bioactive enzyme and drying the same, whereby there is produced a wound dressing in which a majority of said enzyme is bound by sorption and from which said bioactive enzyme is releasable in effective amounts for a period of at least 3 days upon said dressing being brought into contact with a moist surface.

2. The method according to claim 1, wherein said at least one enzyme is trypsin.

3. The method according to claim 1, wherein the degree of oxidation of said textile carrier is less than 0.5% w/w of the textile carrier.

4. The method according to claim 1, wherein said activated carrier is impregnated in a soution of at least one bioactive enzyme and one hormone.

5. The method according to claim 1, wherein said activated carrier is impregnated in a solution of at least two bioactive enzymes.

6. The method according to claim 5, wherein said enzymes are trypsin and lysozyme.

7. The method according to claim 1, wherein said textile carrier is formed of cotton gauze activated by oxidation with sodium periodate to prepare a dialdehyde cellulose.

8. The method according to claim 1, wherein said textile carrier is formed of a knitted fabric from caproamide fibers activated with hydrochloric acid, followed by the addition of glutaric aldehyde groups.

9. A wound dressing prepared according to the method of claim 1 and comprising an activated textile carrier containing between about 0.026 and 0.06 mg-equivalent of aldehyde groups per gram of carrier, said wound dressing being impregnated with at least one bioactive enzyme, whereby said active enzyme is releasable from said wound dressing in effective amounts for a period of at least 3 days upon said dressing being brought into contact with a moist surface.

10. The wound dressing according to claim 9, comprising between about 0.3 and 1.5 mg of bioactive enzyme per gram of carrier.

11. The wound dressing according to claim 10, wherein at least about 80% of the bioactive enzyme is bound to the carrier by sorption and at most about 20% of the bioactive enzyme is bound to the carrier by covalent bonds.

* * * * *